(12) United States Patent
Jaros et al.

(10) Patent No.: US 6,379,715 B2
(45) Date of Patent: *Apr. 30, 2002

(54) METHOD FOR TREATMENT OF PSORIASIS

(76) Inventors: Apolonia Jaros, deceased, late of Bosna (YU); by Bronhilda Miketin, devisee and legal representative, 2019 East 2nd Street, Duluth, MN (US) 55812

( * ) Notice: Subject to any disclaimer, the term of this patent is extended or adjusted under 35 U.S.C. 154(b) by 0 days.

This patent is subject to a terminal disclaimer.

(21) Appl. No.: 09/737,258

(22) Filed: Dec. 14, 2000

Related U.S. Application Data

(63) Continuation-in-part of application No. 09/480,745, filed on Jan. 10, 2000, now Pat. No. 6,316,001.

(51) Int. Cl.7 ............................................... A61K 35/78
(52) U.S. Cl. ...................................................... 424/725
(58) Field of Search ......................................... 424/725

(56) References Cited

U.S. PATENT DOCUMENTS

| | | |
|---|---|---|
| 4,021,573 A | 5/1977 | Lee |
| 5,104,877 A | 4/1992 | Boger |
| 5,122,514 A | 6/1992 | Boger et al. |
| 5,122,536 A | 6/1992 | Perricone |
| 5,165,932 A | 11/1992 | Hovath |
| 5,217,962 A | 6/1993 | Burton et al. |
| 5,476,661 A | 12/1995 | Pillai et al. |
| 5,616,324 A | 4/1997 | Foster et al. |
| 5,747,064 A | 5/1998 | Burnett et al. |
| 5,795,573 A | 8/1998 | Paradise |
| 5,962,010 A | 10/1999 | Greff et al. |

*Primary Examiner*—Raymond Henley, III
(74) *Attorney, Agent, or Firm*—Vidas, Arrett & Steinkraus

(57) ABSTRACT

This invention relates to the natural topical treatment of portions of skin of a person afflicted with psoriasis or other skin disorders such as dry skin, eczema, itchy skin, red skin, itchy eczema, inflamed skin, and/or cracked skin for the removal of itch and the restoration of the affected areas of skin to a normal condition. The natural treatment of a skin disorder initially involves formation of a natural ointment from the ingredients identified as chicken and hen herb; ruta herb; pure unsalted natural butter; and pure natural beeswax. The natural ointment is formed by combination of the ingredients which includes heating and stirring. The ointment is then applied twice daily to affected areas of skin until a natural cure of the skin disorder is obtained.

20 Claims, No Drawings

METHOD FOR TREATMENT OF PSORIASIS

RELATED CASES

This is a continuation-in-part patent application claiming priority to U.S. Utility patent application filed Jan. 10, 2000, application Ser. No. 09/480,745 entitled "Composition and Method for Treatment of Psoriasis", now U.S. Pat. No. 6,316,001.

STATEMENT REGARDING FEDERALLY SPONSORED RESEARCH OR DEVELOPMENT (Not Applicable)

BACKGROUND OF THE INVENTION

The present invention relates to a topical composition for the treatment of psoriasis or other skin disorders such as dry skin, eczema, itchy skin, red skin, itchy eczema, inflamed skin, and/or cracked skin. Psoriasis is generally a skin disease evidenced by the presence of skin elevations and scales which may be silvery in appearance. Psoriasis in general is a disease which accelerates the epidermal proliferation and proliferation of capillaries in the dermal region. In addition, psoriasis frequently results in the evasion of the dermis and epidermis by inflammation of the affected cells.

Areas of skin affected by psoriasis also frequently lose water significantly faster than normal healthy skin. The areas of skin affected by psoriasis therefore tend to have increased metabolic rates which in turn has a negative impact on tissue catabolism and potentially causes muscle wasting.

Psoriasis as a chronic skin disease has been difficult to treat. Psoriasis may affect an individuals skin proximate to elbows, knees, trunk, and scalp. In the past, the treatment of psoriasis has included the use of various chemical agents including but not limited to dihydroxyanthralin, azarabine, colchicine, fluorouracil, methotrexate, methoxsalen, and the use of ultra-violet light. These methods have generally not provided satisfactory treatment of psoriasis for individuals.

Alternatively, therapeutic regimes for the treatment of psoriasis include topical or intra-lesional application of corticosteroids, topical administration of anthralin or keratolytics, and the use of ultra-violet light on the affected areas. As is known in the art, no single therapy is ideal for the treatment of psoriasis and it is extremely rare for a patient to not receive treatment from several different therapeutic alternatives to attempt to prevent relapse and/or remission of the skin disease. In addition, individuals frequently are required to be exposed to increased doses of medication which may magnify side effects adversely affecting the health of the individual.

Psoriasis is a condition which affects approximately two percent of the population. Psoriasis is a condition in which cell proliferation is increased up to 10 times the normal rate for an individual. The skin is the largest portion of the human body which is comprised of cells within three skin layers. Each of the skin layers is in a constant state of growth with the outer layer being formed of predominantly dead tissue which is naturally being discarded at a normal rate. Replacement of cells from underlying layers is accomplished by cell division and maturation where cells move upwardly and outwardly at a rate which varies dependent upon the age, sex, and/or health of an individual. Psoriasis causes an increased turn over of cells which in turn increases the rate of cell growth and cell death. This increased rate of cell growth and cell death may result in injuries and/or disorders which accompany the increased synthesis of all tissue components and further elevate the strain placed upon skin or other tissue and the bio-synthetic capabilities of the cells within the affected area. The method and treatment of psoriasis as disclosed herein preferably slows cell proliferation and naturally treats areas of skin affected by psoriasis. An individuals skin may then heal naturally, minimizing the risk of undesirable side effects and the relapse of the undesirable skin condition.

BRIEF SUMMARY OF THE INVENTION

This invention relates to the natural topical treatment of portions of skin of a person afflicted with psoriasis or other skin disorders such as dry skin, eczema, itchy skin, red skin, itchy eczema, inflamed skin, and/or cracked skin for the removal of itch and the restoration of the affected areas of skin to a normal condition. The natural treatment of psoriasis or other skin disorders initially involves formation of a natural ointment from the ingredients identified as organic chicken and hen herb; organic ruta herb; pure unsalted natural butter; and pure natural beeswax. The natural ointment is formed by combination of the identified-ingredients and the application of heat and stirring. The ointment is then applied twice daily to affected areas of skin until a natural cure of the psoriasis or other undesirable skin condition is achieved.

It is a principal advantage of the present invention to provide a method for treatment of psoriasis or other undesirable skin disorders formed of relatively simple and inexpensive design and operation which is natural and safe and which fulfills the intended purpose of treatment of the symptoms and the provision of a cure for an undesirable skin disease without fear of further injury to individuals.

Another principal advantage of the present invention is the provision of a method for treatment of psoriasis or other undesirable skin disorder which includes a topical treatment completely formed of natural ingredients.

Still another principal advantage of the present invention is the provision of a method for treatment of psoriasis or other undesirable skin disorder which reduces and/or eliminates "itchiness" of skin which is a common symptom/condition of psoriasis or skin disorders.

Still another principal advantage of the present invention is the provision of a method for treatment of psoriasis or other skin disorder which reduces and/or eliminates the undesirable "redness" appearance of skin which is a common symptom/condition of psoriasis or of the skin disorder.

Still another principal advantage of the present invention is the provision of a method for treatment of psoriasis or other skin disorder which reduces and/or eliminates undesirable skin scales which is a common symptom/condition of psoriasis or of the skin disorders.

Still another principal advantage of the present invention is the provision of a method for treatment of psoriasis or other skin disorders which slows moisture loss of affected skin and tissue which is a common symptom/condition of psoriasis or of skin disorders.

Still another principal advantage of the present invention is the provision of a method for treatment of psoriasis or other skin disorder which facilitates the individual layers of skin to return to a normal rate of growth and elevation for the treatment of the skin disorder.

Still another principal advantage of the present invention is the provision of a method for treatment of psoriasis or other skin disorder which minimizes complications encountered by an individual exposed to topical and/or internal medication during treatment received for the undesired skin disease.

Still another principal advantage of the present invention is the provision of a method for treatment of psoriasis or other skin disorder which minimizes relapse or recurrence of the skin disease following completion of a treatment regime.

Still another principal advantage of the present invention is the provision of a method for treatment of psoriasis or other skin disorder which naturally returns moisture to areas of skin affected with the undesirable skin disease.

A feature of the present invention is the provision of a method for treatment of psoriasis or other skin disorder including the topical treatment of an ointment for application to affected areas of skin.

Another feature of the present invention is the provision of a method for treatment of psoriasis or other skin disorder which includes a topical ointment having organic chicken and hen herb.

Still another feature of the present invention is the provision of a method for treatment of psoriasis or other skin disorder which includes a topical ointment having organic ruta herb.

Still another feature of the present invention is the provision of a method for treatment of psoriasis or other skin disorder which includes a topical ointment having pure natural unsalted butter.

Still another feature of the present invention is the provision of a method for treatment of psoriasis or other skin disorder which includes a topical ointment having natural pure bee's wax not candle wax.

Still another feature of the present invention is the provision of a method for treatment of psoriasis or other skin disorder where equal amounts of organic chicken and hen herb and organic ruta herb are mixed with nine times the amount of unsalted natural butter.

Still another feature of the present invention is the provision of a method for treatment of psoriasis or other skin disorder where the organic chicken and hen herb; organic ruta herb; and unsalted natural butter are heated and stirred.

Still another feature of the present invention is the provision of a method for treatment of psoriasis or other skin disorder where pure natural bee's wax is added to the heated mixture of unsalted natural butter, organic chicken and hen herb, and organic ruta herb in a proportion equal to either the amount of organic chicken and hen herb or organic ruta herb.

Still another feature of the present invention is the provision of a method for treatment of psoriasis or other skin disorder where the heated mixture of organic chicken and hen herb, organic ruta herb, unsalted natural butter, and natural pure bee's wax is drained to separate the cream used as a topical ointment for the treatment of the undesirable skin disorder.

Still another feature of the present invention is the provision of a method for treatment of psoriasis or other skin disorder where the cream is used as a natural topical ointment for the treatment of the skin disorder by application into affected areas of skin twice daily until such time as the affected skin has healed.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

The method for treatment of psoriasis or other skin disorders such as dry skin, eczema, itchy skin, red skin, itchy eczema, inflamed skin, and/or cracked skin is disclosed herein. In general, the method for treatment of psoriasis or other skin disorders involves the application of a topical ointment to an affected area of an individuals skin at least once per day and preferably twice per day for treatment of the undesirable skin condition.

The formulation of the ointment initiates with the acquisition of organic chicken and hen herb. The organic chicken and hen herb should be finely chopped for use in formulation of the ointment described herein.

An individual should next obtain an equal amount of organic ruta herb which should also be finely chopped for combination with the organic chicken and hen herb as described above.

Preferably 300 grams of organic chicken and hen herb and 280 grams of organic ruta herb are used as the initial ingredients for the ointment used for treatment of an undesirable skin condition. It should be noted that other portions of organic chicken and hen herb and/or organic ruta herb may be used at the discretion of an individual provided that the ratio of the proportions is maintained for the formulation of the ointment described herein.

An individual next will obtain pure unsalted butter for combination to the chopped organic chicken and hen herb and organic ruta herb. The amount or ratio of pure unsalted butter used for combination to the organic chicken and hen herb and/or organic ruta herb is approximately nine to one. In a preferred embodiment, six pounds, 2.7 kilograms, of pure unsalted butter are utilized for combination with 300 grams of organic chicken and hen herb and 280 grams of organic ruta herb. Again, it should be noted that the amount of pure unsalted butter may vary at the discretion of an individual provided that a ratio of nine portions of pure unsalted butter are used with one portion of organic chicken and hen herb and one portion of organic ruta herb respectively. Therefore, the initial combination of ingredients would include one portion of organic chicken and hen herb, one portion of organic ruta herb, and nine portions of pure unsalted butter.

The ingredients of the pure unsalted butter, organic chicken and hen herb, and organic ruta herb are then heated at approximately 325° F. for a period of one and one-half hours. Preferably the ingredients are heated within a clean porcelain utensil or porcelain coated utensil and are not heated within a steel, stainless steel, and/or aluminum utensil. The use of steel, stainless steel, and/or aluminum utensils may facilitate the burning of the mixture which is undesirable.

During the initial heating of the pure unsalted butter, organic ruta herb, and organic chicken and hen herb the mixture should be stirred every 10 to 15 minutes to reduce risk of burning during the initial heating step.

The stirring and heating of the pure unsalted butter, organic ruta herb, and organic chicken and hen herb will result in the provision of a liquid mixture having a light green color. After heat has been applied to the liquid mixture at approximately 325° F. for a period of 1½ hours, the heat should be reduced to approximately 300° F. for ½ hour allowing the mixture to simmer during this period of time.

The mixture should be continuously stirred every 10 to 15 minutes during the introduction of heat to minimize burning within the utensil.

Approximately 2 hours after the initiation of heat to the mixture, pure natural bee's wax should be added to the light green liquid composition, candle wax should not be used. Preferably 240 grams of pure bee's wax are added to the heated mixture which has preferably been maintained at a simmer at an approximate temperature of 300° F. for 30 minutes. The addition of 240 grams of pure bee's wax represents an equal portion as compared to the organic chicken and hen herb and/or the organic ruta herb as described above. The mixture within the utensil now has approximately one portion of organic chicken and hen herb, one portion of organic ruta herb, nine portions of pure natural unsalted butter, and one portion of pure natural bee's wax.

Following the addition of the pure natural bee's wax the mixture should be cooked for approximately one hour at 300° F. During this period of time, the mixture should be continuously stirred every 10 to 15 minutes to thoroughly mix the pure natural bee's wax within the composition.

Following cooking for approximately 1 hour, the composition should be removed from heat and allowed to stand for approximately 25 minutes. During this 25 minute cooling period the mixture will separate into a liquid phase and a cream phase. The mixture should then be drained through a clean fine tea filter which has not been previously utilized.

The cream obtained through separation of the cream phase from the liquid phase should then be placed within a new and clean container which has previously been sterilized. A preferred type of container may be glass jars and/or plastic jars at the discretion of an individual. Following the placement of the cream ointment within the containers, a suitable device may be used to seal the containers to prevent future contamination.

The containers of the ointment may be stored at room temperature or refrigerated at the discretion of an individual. In the preferred embodiment no preservatives are added to the ointment to facilitate storage.

The ointment may be then extracted from the containers for application to an affected area of skin for the treatment of the undesirable skin condition. Preferably the affected area of skin is treated twice daily, once in the morning and once during the evening to facilitate healing. During use, the ointment is preferably rubbed and/or massaged into an affected area of skin. Itching is normally terminated within three days following the initiation of treatment of the ointment disclosed herein. The topical ointment should be applied to the affected area of skin twice daily until the undesirable skin condition has been cured. The undesirable skin condition treated with the ointment described herein is usually cured within a period of two to three weeks. The affected areas of skin treated with the ointment should not be exposed to soap or shampoo during the course of treatment. The ointment applied to the affected areas of skin should be left on the skin all day and all night until such time as healing is achieved.

An individual using the ointment as described herein should avoid the consumption of caffeine and/or alcohol during treatment of an undesirable skin condition such as psoriasis or other skin disorders such as dry skin, eczema, itchy skin, red skin, itchy eczema, inflamed skin, and/or cracked skin.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. I claim a composition for the topical treatment of skin comprising:
   a) organic chicken and hen herb;
   b) organic ruta herb mixed with said organic chicken and hen herb;
   c) unsalted butter mixed with said organic chicken and hen herb and said organic ruta herb; and
   d) pure bee's wax mixed with said unsalted butter, said organic chicken and hen herb, and said organic ruta herb.

2. The composition according to claim 1, wherein said organic chicken and hen herb and said organic ruta herb are each provided in a first portion which are approximately equal.

3. The composition according to claim 2, wherein said unsalted butter is provided in a second portion which is approximately nine times larger than said first portion.

4. The composition according to claim 3, wherein said pure bee's wax is provided in a third portion which is approximately equal to said first portion.

5. The composition according to claim 4, wherein said organic chicken and hen herb, said organic ruta herb, said unsalted butter, and said pure bee's wax are heated and mixed.

6. The composition according to claim 5, wherein said heated and mixed organic chicken and hen herb, said organic ruta herb, said unsalted butter, and said pure bee's wax are filtered to provide a cream adapted for use as a topical treatment of said skin.

7. The composition according to claim 6, said organic chicken and hen herb comprising 300 grams.

8. The composition according to claim 7, said organic ruta herb comprising 280 grams.

9. The composition according to claim 8, said pure bee's wax comprising 240 grams.

10. The composition according to claim 9, said unsalted butter comprising approximately six pounds (2.7 kilograms).

11. I claim a method for formulation of a topical treatment of skin comprising:
    a) mixing an approximately equal portion of organic chicken and hen herb and organic ruta herb;
    b) adding unsalted butter to said mixed organic chicken and hen herb and said organic ruta herb;
    c) heating said unsalted butter, said organic chicken and hen herb, and said organic ruta herb to a temperature of approximately 325° F. for approximately one and one-half hours;
    d) adding pure bee's wax to said heated unsalted butter, said organic chicken and hen herb, and said organic ruta herb;
    e) cooking said unsalted butter, said organic chicken and hen herb, said organic ruta herb, and said pure bee's wax at a simmer, at a temperature of approximately 300° F. for approximately one hour; and
    g) separating liquid from said unsalted butter, said organic chicken and hen herb, said organic ruta herb, and said pure bee's wax to provide a cream.

12. The method according to claim 11, wherein said organic chicken and hen herb, said organic ruta herb, and said unsalted butter are regularly stirred during said heating and said cooking steps.

13. The method according to claim 12, wherein said organic chicken and hen herb and said organic ruta herb are each provided in a first portion which are approximately equal.

14. The method according to claim 13, wherein said unsalted butter is provided in a second portion which is approximately nine times larger than said first portion.

15. The method according to claim 14, wherein said pure bee's wax is provided in a third portion which is approximately equal to said first portion.

16. I claim a method for treatment of skin comprising:
   a) forming a topical treatment for said skin, said topical treatment comprising:
      i) organic chicken and hen herb;
      ii) organic ruta herb mixed with said organic chicken and hen herb;
      iii) unsalted butter mixed with said organic chicken and hen herb and said organic ruta herb;
      iv) pure bee's was mixed with said unsalted butter, said organic chicken and hen herb, and said organic ruta herb, wherein said organic chicken and hen herb, said organic ruta herb, said unsalted butter, and said pure bee's wax are mixed and heated for formulation of an ointment; and
   b) applying said ointment to said skin at least once per day to treat said skin.

17. The method according to claim 16, said organic chicken and hen herb comprising 300 grams.

18. The method according to claim 17, said organic ruta herb comprising 280 grams.

19. The method according to claim 18, said pure bee's wax comprising 240 grams.

20. The method according to claim 19, said unsalted butter comprising six pounds (2.7 kilograms).

* * * * *